United States Patent
Eglin et al.

(10) Patent No.: US 6,448,196 B1
(45) Date of Patent: Sep. 10, 2002

(54) POLYMERIZATION CATALYST AND POLYMERIZATION PROCESS

(75) Inventors: David Eglin, Torcy (FR); Jean de la Cro Habimana, Braine le Comte (BE); Peter Hupfield, Carmarthen (GB); Avril Surgenor, Cardiff (GB); Richard Taylor, Barry (GB)

(73) Assignee: Dow Corning Limited, Barry (GB)

( * ) Notice: Subject to any disclaimer, the term of this patent is extended or adjusted under 35 U.S.C. 154(b) by 0 days.

(21) Appl. No.: 09/458,244

(22) Filed: Dec. 9, 1999

(30) Foreign Application Priority Data

Dec. 9, 1998 (GB) ............................................. 9827069

(51) Int. Cl.[7] ........................... B01J 27/14; C08G 77/08
(52) U.S. Cl. ......................................... 502/167; 528/23
(58) Field of Search ............................ 528/23; 502/167

(56) References Cited

U.S. PATENT DOCUMENTS

| | | | |
|---|---|---|---|
| 2,990,419 A | 6/1961 | Nitzsche et al. | 556/401 |
| 3,549,680 A | 12/1970 | Wegehaupt et al. | 556/451 |
| 4,902,813 A | 2/1990 | Wegehaupt et al. | 556/459 |
| 6,054,548 A * | 4/2000 | Currie et al. | 528/23 |
| 6,184,330 B1 * | 2/2001 | Currie et al. | 528/23 |
| 6,221,993 B1 | 4/2001 | Currie et al. | 528/23 |

FOREIGN PATENT DOCUMENTS

| | | | |
|---|---|---|---|
| EP | 791600 A1 | 2/1997 | |
| EP | 879838 A2 | 11/1998 | |
| EP | 879 838 A2 * | 11/1998 | |
| EP | 0982346 A1 | 3/2000 | C08G/77/08 |
| GB | 2252969 A | 8/1992 | C01B/21/098 |

OTHER PUBLICATIONS

Reinhard Schwesinger, et. al., "Extremely Strong, Uncharged Auxiliary Bases; Monomeric and Polymer–Supported Polyaminophosphazenes (P2–P5)", Liebigs Ann. 1996, pp. 1055–1081.

* cited by examiner

*Primary Examiner*—Margaret G. Moore
(74) *Attorney, Agent, or Firm*—Jennifer S. Warren; Timothy J. Troy

(57) ABSTRACT

Siloxanes are polymerized by equilibration, condensation and/or ring-opening polymerization using a phosphazene base catalyst. A linear phosphazene base catalyst of the general formula $$\{(R_2N)_3P=N-(P(NR_2)=N)_n-P^+(NR_2)_3\}X^- \quad (1)$$

wherein R denotes a $C_{1-10}$ hydrocarbon or wherein two R groups on one N atom form with the N atom a heterocyclic group, X denotes an anion and n is from 1 to 10 is prepared by reacting a linear phosphonitrile halide compound with a secondary amine or a salt of a secondary amine or a metal amide thereof to form an aminated phosphazene material, followed by an ion exchange reaction replacing the anion with a nucleophile.

8 Claims, No Drawings

POLYMERIZATION CATALYST AND POLYMERIZATION PROCESS

FIELD OF THE INVENTION

The present invention relates to catalysts for the polymerization of siloxanes and to the use of such catalysts for the polymerization of siloxanes via ring opening of cyclic siloxanes or via condensation of silanol or alkoxy end-blocked siloxane materials or via equilibration of siloxanes. The present invention is more particularly related to phosphazene base catalysts, and especially linear phosphazene base catalysts for said polymerization.

BACKGROUND OF THE INVENTION

In EP0860461-A, there is described a process for the ring-opening polymerization of cyclosiloxanes, which comprises contacting a cyclosiloxane with 1 to 500 ppm of a phosphazene base, by weight of cyclosiloxane, in the presence of water. The phosphazene base catalyst described in that specification is preferably selected from the general formulae:

$$((R^1{}_2)_3P{=}N{-})_x(R^1{}_2N)_{3-x}P{=}NR^2$$

$$\{((R^1{}_2N)_3P{=}N{-})_x(R^1{}_2N)_{3-x}P{-}N\,(H)R^2\}^+(A)^-$$

and $$\{((R^1{}_2N)_3P{=}N{-})_y(R^1{}_2N)_{4-y}P\}^+(A)^-$$

in which each $R^1$ independently is hydrogen or an optionally substituted hydrocarbon group, or in which two $R^1$ groups bonded to the same N-atom may be linked to complete heterocyclic ring; $R^2$ is hydrogen or an optionally substituted hydrocarbon group; x is 1, 2 or 3; y is 1, 2, 3 or 4; and A is an anion.

EP0879838-A describes a process of preparing a polymer which comprises conducting ring-opening polymerization of a 4- to 10-membered cyclic monomer in the presence of a phosphazenium salt catalyst of an active hydrogen compound represented by the formula

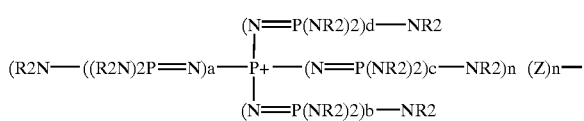

Although these catalysts are very useful materials, the manufacturing process for many of them is often complex, using in some cases as many as 25 raw materials, solvents and intermediates in up to 12 key process steps, including low temperature manufacture, distillation, filtration, recrystallization and ion-exchange. This makes the process difficult, expensive and time consuming.

We have now surprisingly found that there is no need to make such complex phosphazene base materials for the polymerization of siloxanes. Indeed a more simple structure of phosphazene base materials, in the form of linear polyamino phosphazenium salts containing nucleophilic anions are found to be excellent catalysts for the polymerization of siloxanes, whether by ring-opening polymerization of cyclic siloxanes or by condensation of silanol or silicon-alkoxy end-blocked siloxanes. These linear phosphazene base materials can be made in a much more economic and simple process.

SUMMARY OF THE INVENTION

This invention provides a linear phosphazene base catalyst of the general formula,

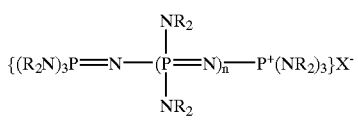

(1)

wherein R denotes a hydrocarbon having up to 10 carbon atoms or wherein the two R groups on each N atom form with the N atom a heterocyclic group, X denotes an anion and n has an average value of from 1.2 to 10.

This invention also provides a process for making a linear phosphazene base catalyst comprising reacting a linear phosphonitrile halide compound with a compound selected from secondary amines and salts and metal amides thereof to form an aminated phosphazene material, followed by reacting the aminated phosphazene material in an ion exchange reaction replacing the anion of the aminated phosphazene material with a nucleophile.

This invention further provides a process of polymerization of siloxanes via equilibration and/or condensation comprising contacting the siloxanes with the linear phosphazene base catalyst of formula (1).

DETAILED DESCRIPTION OF THE INVENTION

According to the present invention, a linear phosphazene base catalyst has the general formula

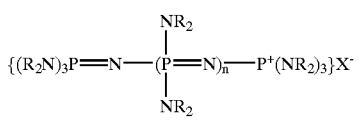

(1)

wherein R denotes a hydrocarbon having 1 to 10 carbon atoms or wherein the two R groups on one N atom form with the N atom a heterocyclic group, X denotes an anion and n is from 1 to 10.

According to one aspect of the invention, a process for making a linear phosphazene base catalyst comprises reacting a linear phosphonitrile halide compound with a secondary amine or a salt of a secondary amine or a metal amide thereof to form an aminated phosphazene material, followed by an ion exchange reaction replacing the anion with a nucleophile.

According to another aspect of the invention, siloxanes are polymerized via equilibration and/or condensation in the presence of a linear phosphazene base catalyst of formula (1).

The process for making the linear phosphazene base catalysts of formula (1) uses as its main ingredient a phosphonitrile halide, preferably a phosphonitrile chloride. Using a phosphonitrile halide, which is already an ionic material, renders the manufacture of the phosphazene base catalysts simpler. Phosphonitrile halides are known and have been described in a number of patent specifications, which are hereby included by reference. Many of these patent specifications describe the use of these halides as catalysts for the polymerization of certain types of siloxanes. For example, GB 910513 discloses phosphonitrile halide catalysts for use in a process for the manufacture of stabilized high viscosity polyorganosiloxane oils and in US 3549680 phosphonitrile halide catalysts are employed in rearrangement reactions. EP 319978 describes chlorophosphonitrile catalysts for use in a process for the preparation of polydiorganosiloxanes containing a silicon-bonded hydroxyl group in each of the terminal units. Other phosphonitrile halide catalysts have been described in GB 2252969. Examples of suitable phosphonitrile halides include $(Cl_3P=N-(P=NCl_2)_n-PCl_3)^+Z^-$, wherein Z— is preferably $Cl^-$ or $PCl_6^-$ and n is 1–10, preferably 1 to 5.

Processes for making these phosphonitrile halide materials are described in many of the above mentioned specifications. One useful process includes the reaction of $PCl_5$ with $NH_4Cl$ in the presence of a suitable solvent. In an even more useful process, described in our copending application GB9827055.6, the ammonium chloride is replaced with hexamethyldisilazane. This process comprises a first step of reacting $PX_5$ and a disilazane under cooling in an inert non-chlorinated solvent and a second step of heating the reaction mixture to at least 50° C. for a time sufficient to produce the phosphonitrile halide. This process is particularly preferred as the phosphazene halide thus produced has a reduced level of phosphonitrile chloride having only 2 phosphorus atoms present. It has been found that phosphazene bases having only 2 phosphorus atoms, which could be made according to the present invention (formula (1) where the value of n would be 0) are less active as a catalyst for the polymerization of siloxanes.

The above processes generally produce a mixture of phosphonitrile halides; a mixture of phosphonitrile halides can be used as a starting material in the process of the invention, producing a mixture of phosphazene base catalysts. Mixtures of catalysts of formula (1) in which the average value of n is above 1 are preferred catalysts which cannot be prepared by known methods. Particularly preferred linear phosphazene base catalysts are those of formula (1) in which the average value of n is at least 1.2 up to 5 or 10, especially from 1.5 or 1.8 up to 3, as these have been found to be the most effective catalytic species for the polymerization of siloxanes.

The process for preparing the phosphazene base catalyst according to the invention is much less complex than the processes required previously for the making of phosphazene bases, for example those described e.g. by Schwesinger et al. in Liebig. Ann. 1996, 1055–1081. The catalysts according to the present invention can be made by merely reacting the phosphonitrile halide, preferably chloride, with a secondary amine of the formula $R_2NH$, wherein R is selected from hydrocarbon groups having up to 10 carbon atoms, for example methyl, or the two R groups which are found on a single N atom form with the nitrogen atom a heterocyclic group, e.g. a pyrollidine group, a pyrrole group or a pyridine group for the polymerization of siloxanes. Suitable preferred secondary amines include dimethylamine and pyrollidine. Preferably the reaction is carried out in the presence of a material which is able to capture the exchanged halides, e.g. a tertiary amine such as triethylamine. The resulting by-product (e.g. triethyl ammonium chloride) can then be removed from the reaction mixture, e.g. by filtration. The reaction may be carried out in the presence of a suitable solvent for the phosphonitrile chloride and linear phosphazene base. Suitable solvents include aromatic solvents such as toluene.

The amine can be added in its salt form, e.g. dimethylamine hydrochloride, although this is not generally preferred since less common solvents may be required.

The amine can be in the form of its metal amide. For example it can be reacted with an alkali metal or alkyl alkali metal compound, particularly an alkyl lithium compound such as n-butyl lithium, to form the metal amide. After reaction with the phosphonitrile halide, the alkali metal halide can be removed by filtration.

The groups R in the linear ionic phosphazene base catalyst of formula (1) are derived from the secondary amine R2NH. The two R groups on each N atom can be the same or different, e.g. the secondary amine can be methylethylamine. The NR2 groups in the phosphazene base are generally the same as each other although they can be different if a mixture of secondary amines is used.

The linear phosphazene material which is formed this way is generally in the form of a salt with the anion Z—, e.g. Cl— or PCl6—, derived from the phosphonitrile halide. This is preferably treated in an ion exchange reaction (preferably by passing over an ion exchange resin) whereby the anion is replaced with a basic nucleophile X— to form a stronger base. The counterion X is preferably hydroxyl (hydroxide), an alkoxy (alkoxide) group having up to 25 carbon atoms, or silanolate, fluoride, carbonate or bicarbonate. The phosphazene is preferably dispersed in a suitable medium prior to passing through an ion exchange system. Suitable media include water, alcohol and mixtures thereof.

Polymerization of siloxanes according to the present invention includes equilibration polymerization, ring opening polymerization of cyclic siloxanes, and condensation polymerization, which is based on the condensation of silanol groups, which may be present in the siloxanes, or which may be formed there in situ, e.g. by hydrolysis of silicon-bonded hydrolyzable groups such as alkoxy groups.

The starting material for ring-opening polymerization is a cyclosiloxane (also known as a cyclic siloxane). Cyclic siloxanes which are useful are well known and commercially available materials. They have the general formula $(R^3_2SiO)_m$, wherein $R^3$ denotes hydrogen or an optionally substituted alkyl, alkenyl, aryl, alkaryl or aralkyl group having up to 8 carbon atoms, m denotes an integer with a value of from 3 to 12. $R^3$ can be substituted, e.g. by halogen such as fluorine or chlorine. The alkyl group can be, for example, methyl, ethyl, n-propyl, trifluoropropyl, n-butyl, sec-butyl, and tert-butyl. The alkenyl group can be, for example, vinyl, allyl, propenyl, and butenyl. The aryl and aralkyl groups can be, for example, phenyl, tolyl, and benzoyl. The preferred groups are methyl, ethyl, phenyl, vinyl, and trifluoropropyl. Preferably at least 80% of all $R^3$ groups are methyl or phenyl groups, most preferably methyl. It is most preferred that substantially all $R^3$ groups are methyl groups. Preferably the value of m is from 3 to 6, most preferably 4 or 5. Examples of suitable cyclic siloxanes are octamethyl cyclotetrasiloxane, decamethyl cyclopentasiloxane, cyclopenta (methylvinyl) siloxane, cyclotetra (phenylmethyl) siloxane and cyclopenta methylhydrosiloxane. One particularly suitable commercially available material is a mixture of octamethylcyclotetrasiloxane and decamethylcyclopentasiloxane.

The starting material for equilibration polymerization can be cyclic siloxanes as described above and/or any polydiorganosiloxane material having units of the general formula $R'_aSiO_{4-a/2}$ (2) wherein R' denotes a hydrogen atom, a hydrocarbon group having from 1 to 18 carbon atoms, a substituted hydrocarbon group having from 1 to 18 carbon atoms or a hydrocarbonoxy group having up to 18 carbon atoms and a has on average a value of from 1 to 3, preferably 1.8 to 2.2. Preferably the polydiorganosiloxanes are polydialkylsiloxanes, and most preferably polydimethylsiloxanes. They are preferably substantially linear materials, which are end-blocked with a siloxane group of the formula $R''_3SiO_{1/2}$, wherein R" is R' or hydroxyl.

Starting materials for the condensation reaction of silanol containing siloxanes are polyorganosiloxanes having silicon-bonded hydroxyl groups or hydrolyzable groups such as alkoxy groups, which may form silanol groups in situ. These include, for example, polyorganosiloxanes having the a general formula (3):

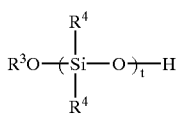

(3)

In formula (3), $R^3$ denotes hydrogen or an optionally substituted alkyl, alkenyl, aryl, alkaryl or aralkyl group having up to 8 carbon atoms, each R4 denotes a monovalent hydrocarbon group preferably having 1 to 18 carbon atoms or halogenated hydrocarbon group preferably having 1 to 18 carbon atoms and t is an integer having a value of from at least 2. Preferably $R^4$ denotes an alkyl group having from 1 to 6 carbon atoms and more preferably a methyl group. The value of t is preferably such that the average viscosity of the polyorganosiloxanes does not exceed 200 mm$^2$/s at 25° C.

Polyorganosiloxanes having terminal silicon-bonded hydroxyl groups are well known and are commercially available. Preferred polyorganosiloxanes have one silicon-bonded hydroxyl group in each terminal group and have at least 80% of the $R^4$ groups denote a methyl group. Suitable polyorganosiloxanes for use as reagents in a polymerization process in which the catalysts of the invention are used include polydiorganosiloxanes having terminal hydroxydiorganosiloxane units, e.g. hydroxyldimethyl siloxane end-blocked polydimethylsiloxanes, hydroxyldimethyl siloxane end-blocked polydimethyl poly-methylphenyl siloxane copolymers, triorganosiloxane end-blocked polydimethylsiloxanes, e.g. trimethylsiloxane end-blocked polydimethylsiloxanes and cyclic polydiorganosiloxanes, e.g. polydimethylcyclosiloxanes.

Thus the process according to the invention is useful for making polyorganosiloxanes having units of the general formula $R'_aSiO_4a/2$ (2) wherein R' and a are as described above. Preferably at least 80% of all R' groups are alkyl or aryl groups, more preferably methyl groups. Most preferably substantially all R' groups are alkyl or aryl groups, especially methyl groups. The polyorganosiloxanes are preferably those in which the value of a is 2 for practically all units, except for the end-blocking units, and the siloxanes are substantially linear polymers of the general formula $R''(R'_2SiO)_pSiR'_2R''$ (3) wherein R' and R" are as defined above and p is an integer. It is, however, also possible that small amounts of units wherein the value of a denotes 0 or 1 are present. Polymers with such units in the chain would have a small amount of branching present. Preferably R" denotes a hydroxyl group or an alkyl or aryl group, e.g. methyl or phenyl. The viscosity of the polyorganosiloxanes which may be produced by the process using a catalyst according to the present invention may be in the range of from 1000 to many millions mm$^2$/s at 25° C., depending on the reaction conditions and raw materials used in the method of the invention.

The process according to the invention can be used to make a whole range of siloxane polymers, including liquid siloxane polymers and gums of high molecular weight, for example from 1×10$^6$ to 100×10$^6$. The molecular weight of silicone polymers is effected by the concentration of end groups and in the absence of added end groups is determined by the catalyst concentration. The catalyst used in the present invention has sufficient activity to enable the formation of polymers in a reasonable time at a low catalyst concentration.

We have found that phosphazene base catalysts according to the invention when used at very low concentrations (2–500ppm) based on the weight of the cyclosiloxanes produce polymers with very high molecular weights (1,000,000–100,000,000) very quickly (10 seconds to 8 hours) even at moderate to low temperatures (20–170° C.). Molecular weight changes during polymerization can be monitored by sampling the reaction during polymerization, and analyzing each sample by gel permeation chromatography to determine the molecular weight. Polymers of very high molecular weights can be obtained because of the very low catalyst concentrations needed for the polymerization, with the result that the molecular weight of the polymer produced is dependent on the end group concentration which is equal to the catalyst concentration. However, we have found that at very low catalyst concentrations, such as 2 ppm, the molecular weight obtained increases with reaction time. The process may be limited by diffusion of the catalyst, which is very slow in these high molecular weight polymers.

As an alternative to high molecular weight gums, the process according to the invention can also be used in equilibration reactions to produce silicone fluids, for example in the viscosity range at 25° C. of from 1 to 150,000 mm$^2$/s. An end-blocker is added in a proportion calculated to produce the desired molecular weight of polymer. Suitable end-blockers are, for example, polysiloxanes, particularly linear polysiloxanes, in the molecular weight range from 160 upwards, in particular polydimethylsiloxanes of the general formula MD$_x$M where M is $(CH_3)_3SiO_{1/2}$, D is —Si(CH$_3$)$_2$O$_{2/2}$— and x has a value of from 0 to 20. The end-blocker may have one or more functional groups such as hydroxyl, vinyl or hydrogen. Water also acts as a end-blocker, with the introduction of hydroxyl functional groups. We have found that the use of an end-blocker gives better control of the molecular weight and polydispersity of the siloxane polymer produced than other methods of control such as stopping the polymerization reaction before completion.

The catalysts of the invention may be used at a concentration of from 1 to 500 ppm by weight based on the total weight of the organosiloxanes used as reagents in a polymerization process. Preferably from 5 to 150 ppm by weight are used, most preferably from 5 to 50 ppm. The amount of catalyst used in the method of the invention may be reduced when the temperature at which the organosilicon compounds and the catalyst are contacted is increased. The method of the invention may conveniently be carried out at room temperature or at temperatures as high as 250° C. or 300° C. or even higher. The preferred temperature range may be from 50 to 170° C.

The polymerization can be carried out in bulk or in the presence of a solvent. Suitable solvents are liquid hydrocarbons or silicone fluids. The phosphazene base catalyst can be diluted in a solvent such as toluene or dispersed in a silicone fluid such as polydiorganosiloxanes.

The polymerization reaction can be carried out at ambient temperature or under heating. Heating, for example to 100° C. or higher, is appropriate when the catalyst activity has been moderated as described below. The time taken for polymerization will depend on the activity of the catalyst in the chosen system, and on the desired polymer product. In the absence of moderation, the phosphazene base catalysts are sufficiently active to convert cyclosiloxanes such as octamethylcyclotetrasiloxane to high molecular weight polysiloxane gums within a few seconds.

When the desired polymer has been formed, it is usually desirable to neutralize the catalyst to stabilize the product and prevent any further reaction. Suitable neutralizing agents are acids such as acetic acid, silyl phosphate, polyacrylic acid chlorine substituted silanes, silyl phosphonate or carbon dioxide.

We have found during preparation of the phosphazene base catalysts that air reacts very rapidly with the catalyst solutions giving a hazy material which eventually leads to an insoluble liquid phase. This is believed to be due to the reaction of the catalyst with $CO_2$ to form a carbonate salt. We have also found that this deactivation of the catalyst can be reversed e.g. by heating, purging with inert gas or subjecting the mixture to reduced pressure. This makes it possible to moderate or control the polymerization reaction. This is particularly advantageous in view of the very rapid reaction which occurs when the catalyst is not moderated. Because of the very low levels of catalyst employed in these reactions (which can be as low as 1–10 ppm), the reaction with $CO_2$ needs to be taken into account to control the reaction and obtain reproducible results.

We have also found that polymerization can be prevented by exposing a mixture of siloxane and phosphazene base catalyst to air and/or $CO_2$ or larger amounts of water. The polymerization can then be initiated ("command polymerization") simply by removing the air and/or $CO_2$ or the water e.g. by heating the mixture (e.g. to 100° C.–170° C. for a few minutes).

EXAMPLES

There now follow a number of examples which clarify the invention. All parts and percentages are given by weight unless otherwise indicated and all viscosities are given at 25° C.

Synthesis Example 1
I. Synthesis of Linear Phosphonitrilic Chlorides.

Phosphorous pentachloride (0.237 moles) was charged to a three necked flask fitted with dropping funnel, thermometer and condenser. To this was added anhydrous toluene and the flask contents cooled to −50° C. Hexamethyldisilazane (HMDZ) (0.191 moles) was added dropwise and upon addition the flask contents were allowed to warm to room temperature, upon which they were refluxed at a reaction temperature of 120° C. for two hours. The solvent was then removed under reduced pressure and the solid residue stored under nitrogen. NMR analysis showed the material to have the following average structure $(Cl_3P\text{—}N\text{—}(P\text{=}NCl_2)_{1.8}\text{—}PCl_3)^+(PCl_6)^-$. Table 1 shows how the structure of the linear phosphonitrilic chloride can be tailored through experimental conditions (temperature of addition of HMDZ, reaction temperature and reaction time).

TABLE 1

| Ex | Ratio $PCl_5$/HMDZ | HMDZ add. t °C. | Reaction t °C. | Reaction Time (min) | % P2 | % P3 | % P4 | %> P4 | % Pc | % HP |
|---|---|---|---|---|---|---|---|---|---|---|
| a | 3.1:1 | 20 | 100 | 60 | 2 | 9 | 25 | 43 | 21 | — |
| b | 3:2 | 20 | 120 | 60 | — | 10 | 39 | 20 | 13 | 8 |
| c | 3:2.8 | −50 | 50 | 30 | — | 5 | 5 | 70 | 10 | 10 |
| d | 3.5:2 | 20 | 120 | 180 | 27 | 5 | 6 | — | 56 | 6 |
| e | 3:2 | −50 | 120 | 120 | 2 | 18 | 40 | 26 | 1 | 13 |
| f | 3:2 | −40 | 60 | 60 | 40 | 25 | 23 | 10 | 2 | — |
| g | 3:2 | −5 | 70 | 60 | 5 | 40 | 30 | 15 | 3 | 7 |
| h | 3:2 | 0 | 70 | 60 | 28 | 37 | 17 | 18 | — | — |
| I | 3:2 | 0 | 70 | 40 | 15 | 49 | 23 | 10 | 2 | 1 |
| j | 3:2 | 2 | 40 | 60 | 14 | 60 | 14 | 6 | 6 | — |

Key:
$(Cl_3P\text{—}N\text{—}(P\text{=}NCl_2)_n\text{—}PCl_3]^+PCl_6$
for P2: n = 0; for P3: n = 1; for P4: n = 2
Pc is a cyclic trimer $(P\text{=}NCl_2)_3$ and HP is the Hydrolysis product II. Synthesis of Polyaminophosphazenium Hydroxide.

Toluene and a linear phosphonitrilic chloride (0.023 moles from example I.e, average n=1.8) were charged to a three necked flask fitted with a thermometer, condenser and dropping funnel. The reaction mixture was allowed to cool to −50° C. and a mixture of triethylamine and pyrollidine (0.28 moles each) was added dropwise. The reaction mixture was then allowed to warm to room temperature upon which it was heated to approximately 60° C. for up to 40 hours. The orange solution was filtered to remove triethylammonium chloride and then washed with toluene. The toluene was then removed under reduced pressure to yield an orange oil. The oil was then dispersed in distilled water and methanol (1:1) and passed through a basic (OH⁻) anion exchange resin. The water and methanol were then removed under reduced pressure to yield a basic oil in approximately 90% yield. This comprised a phosphazene base of formula (1) where R2N- is apyrrolidine group and average n=1.8.

Synthesis Example 2
Synthesis of Model Compound 1,1,1,3,3,5,5,5-octapyrollidinium Phosphazenium Hydroxide.

$Cl_3PNPCl_2O$ (0.092 moles) and $(Cl_3PNPCl_3)^+(PC_6)^{31}$ (0.0092 moles), synthesized using known procedures were charged to a three necked flask fitted with stirrer, thermometer and condenser. To this was added 1,2,4-trichlorobenzene and the mixture was heated to 195° C. for up to 30 hours. The crude product was dissolved in tetrachloroethane and precipitated by repeat additions of carbon tetrachloride. A white crystalline product was formed, which was then washed with petroleum ether and dried under vacuum (65% yield). Conversion to the phosphazenium hydroxide was carried out by dispersing the crystalline material in distilled water and methanol (1:1) and passing it through a basic (OH⁻) anion exchange resin. The water and methanol were then removed under reduced pressure.

Polymerization Example 1

A α,ω-silanol terminated polydimethylsiloxane (11,046 ppm OH; 75.8 mm²/s) was charged to a reaction vessel. This was heated to 100° C. under reduced pressure (40 mbar) in the presence of 110 ppm of a linear polyaminophosphazenium hydroxide catalyst $(Py_3\text{—}N\text{—}(P\text{=}NPy_2)_{1.8}\text{—}PPy_3)^+$ OH⁻ where Py=pyrrolidine prepared in Synthesis Example 1. After a reaction time of 15 minutes, a polymer with a viscosity of approximately 166,000 cs at 25° C. was obtained with a nonvolatile content of 90.6%. Residual silanol was determined to be 314.5 ppm.

Polymerization Example 2

A silanol terminated polydimethylsiloxane (11,046 ppm OH; 75.8 cs) was charged to a reaction vessel. This was heated to 100° C. under reduced pressure (40 mbar) in the presence of a linear polyaminophosphazenium hydroxide catalyst as used in Polymerization Example 1. After a reaction time of 20 minutes, a polymer with a viscosity of approximately 244,000 cs was obtained with a NVC of 91.1%. Residual silanol was determined to be 278.9 ppm.

Polymerization Example 3

A 50/50 mixture of silanol end-blocked polydimethylsiloxanes having a viscosity of 14 mm²/s and cyclodimethylsiloxanes, (96.1 g) and a polydimethyl siloxane end-blocker having a viscosity at 25° C. of 5 mm²/s, (3.9 g) were mixed together in a reaction vessel and the reaction mixture heated to 100° C. and pressure of 150 mbar. At that temperature phosphazene base catalyst containing a mixture of polyaminophosphazenium hydroxides prepared by Synthesis Example 1, (330 ppm) was added. After 2 hours the reaction was cooled and neutralized prior to stripping for 1 hr at 145° C. under greatly reduced pressure. The final product had a viscosity at 25° C. of 718 mm²/s, a nonvolatile content of 96.0% and a residual silanol content of 115 ppm.

Polymerization Examples 4–10 x g of octamethylcyclotetrasiloxane and y g of polydimethylsiloxane end-blocker with a viscosity of 100 mm²/s fluid, with a water content of approximately 60 ppm, were placed in a reaction vessel under nitrogen. The reaction mixture was heated to 100° C. and held for thirty minutes under reduced pressure (600 mbar) to remove dissolved $CO_2$. The reaction mixture was then placed under a nitrogen atmosphere, heated to t° C. upon which z ppm 1,1,1,3,3,5,5,5-octapyrollidinium phosphazenium hydroxide was added. After n minutes the reaction mixture was neutralized yielding a polymer with a Non-Volatile Content NVC %. After de-volatilization, a polymer with a viscosity of approximately η mm²/s was obtained with a final NVC %. Values of x, y, z, n, η, NVC and final NVC are given in Table 2.

TABLE 2

| Example | x | y | t ° C. | z | n | NVC | η | Final NVC |
|---|---|---|---|---|---|---|---|---|
| 4 | 250 | 7.53 | 100 | 50 | 5 | 87% | 426000 | 98% |
| 5 | 90 | 10.0 | 130 | 25 | 5 | 86% | 10700 | 98% |
| 6 | 90 | 10.0 | 130 | 13 | 5 | 87% | 12000 | 96% |
| 7 | 90 | 10.0 | 170 | 50 | 1 | 86% | 9900 | 98% |
| 8 | 90 | 10.0 | 170 | 50 | .3 | 85% | 7400 | 96% |
| 9 | 90 | 10.0 | 170 | 5 | 1 | 85% | 7500 | 96% |
| 10 | 90 | 10.0 | 170 | 5 | .3 | 85% | 10900 | 98% |

Polymerization Example 11

Silanol end-blocked polydimethylsiloxane having a viscosity of 60 mm²/s (57.3 g), octamethylcyclodisiloxane (38.8 g) and a polydimethylsiloxane end-blocker having a viscosity of 5 mm²/s (3.9 g) were mixed together in a reaction vessel. The reagents were heated up to 130° C. under vacuum and 1,1,1,3,3,5,5,5-octapyrollidium phosphonitrile hydroxide (100 ppm) catalyst was added at that temperature. After 30 minutes the reaction was allowed to cool and the mixture was neutralized with stoichiometric excess bis-(dimethylvinylsilyl) vinyl phosphonate. The pre-stripped polymer had a nonvolatile content of 87.8%. After stripping at 145° C. for 1 hour, the final product had a viscosity of 773 mm²/s and nonvolatile content of 99.5%.

Polymerization Example 12

Silanol end-blocked polydimethylsiloxane having a viscosity of 60 mm²/s (83.4 g ), a 50/50 mixture of low silanol-end-blocked polydimethyl siloxanes having a viscosity of 14 mm²/s and cyclodimethylsiloxanes, (12.7 g) and a polydimethylsiloxane end-blocker having a viscosity of 5 mm²/s (3.9 g) were mixed together in a reaction vessel and the reaction mixture was heated to 130° C. at a reduced pressure of 400 mbar. 1,1,1,3,3,5,5,5-octapyrollidium phosphonitrile hydroxide (100 ppm) catalyst was added at that temperature. After 5 minutes a sample was removed for silanol analysis (160 ppm —OH). After 1 hour a stoichiometric excess of a neutralization agent bis-(dimethylvinylsilyl) vinyl phosphonate, was added and the mixture was stirred for 30 minutes. After stripping at 145° C. for 1 hour the final product had viscosity 420 mm²/s and a nonvolatile content of 97%.

Synthesis Example 3

Toluene and a linear phosphonitrilic chloride (0.030 moles from example I.c, containing a mixture of species from P3+ to P11+) were charged to a three necked flask fitted with a thermometer, condenser and dropping funnel. The reaction mixture was allowed to cool to −20° C. and dimethylamine bubbled through the reaction mixture for one hour, after which the reaction mixture was allowed to warm to room temperature upon which it was left stirring under nitrogen for a further 24 hours. The reaction mixture was then filtered and the filtrate washed with 50 ml toluene. The solvent was then removed under reduced pressure to yield a wax like product.

The product ($3 \times 10^{-3}$ moles) was dissolved in water (10 ml) and heated to reflux upon which a solution of aqueous sodium hydroxide (0.019 moles) was added. Upon addition the reaction was held at reflux for a further three hours. The reaction mixture was then cooled to room temperature and washed with water (100 ml) and hexane (100 ml). The product was then placed under vacuum to remove solvent and water residues resulting in an overall yield of poly (dimethylamino)phosphazenium hydroxide of approximately Synthesis Example 4

I Synthesis of Linear Phosphonitrilic Chlorides.

Phosphorus pentachloride (0.030 moles), ammonium chloride (0.015 moles) and dichlorobenzene (30 ml) were charged to a three necked flask fitted with a thermometer and condenser. The reaction mixture was then heated to reflux under nitrogen for twelve hours, upon which the dichlorobenzene was removed under reduced pressure to yield a linear phosphonitrilic chloride rich in $P_3^+$ and containing $P_4^+$.

II Synthesis of Polyaminophosphazenium Chloride

Toluene and the linear phosphonitrilic chloride of Synthesis Example 4.I (0.030 moles from example add2a) were charged to a three necked flask fitted with a stirrer, condenser and thermometer. The reaction mixture was allowed to cool to −20° C. and dimethylamine bubbled through the reaction mixture for one hour, after which the reaction mixture was allowed to warm to room temperature upon which it was left stirring under nitrogen for a further three hours. The reaction mixture was then filtered and the filtrate washed with 50 ml toluene. The solvent was then removed under reduced pressure to yield a pale yellow oil.

III Synthesis of Polyaminophosphazenium Hydroxide

The oil from Synthesis Example 4.II was dispersed in distilled water and methanol (1:1) and passed through a basic (OH⁻) anion exchange resin. The water and methanol were then removed under reduced pressure to yield a basic oil in approximately 93% yield.

Synthesis Example 5

I Synthesis of Polyaminophosphazenium Chloride

Toluene and the linear phosphonitrilic chloride of Synthesis Example 4.I (0.030 moles) were charged to a three necked flask fitted with a stirrer, condenser and thermometer and dropping funnel. The reaction mixture was allowed to cool to −50° C. and a mixture of triethylamine and pyrollidine (0.032 moles each) was added dropwise. The reaction mixture was then allowed to warm to room temperature upon which it was heated to approximately 60° C. for up to 40 hours. The orange solution was filtered to remove triethylammonium chloride and then washed with toluene. The toluene was then removed under reduced pressure to yield an orange oil.

II Synthesis of Polyphosphazenium Hydroxide

The oil was then dispersed in distilled water and methanol (1:1) and passed through a basic (OH⁻) anion exchange resin. The water and methanol were then removed under reduced pressure to yield a basic oil comprising polypyrrolidinophosphazenium hydroxide in approximately 93% yield.

Synthesis Example 6
Polyaminophosphazenium Fluoride

The linear polyaminophosphazenium chloride prepared in Synthesis Example 5.I (0.0058 moles), methanol (5 ml) and sodium tetrafluoroborate were charged to a three necked flask fitted with a condenser and thermometer. The reaction mixture was then heated to reflux for two hours. The solution was then filtered and the solvent removed under reduced pressure to yield the linear polyaminophosphazenium tetrafluoroborate complex.

The linear polyaminophosphazenium tetrafluoroborate (0.002 moles) was charged to a three necked flask fitted with a thermometer and condenser. To this was added methanol (2 ml) and potassium fluoride (0.004 moles) and the reaction mixture stirred for two hours at room temperature. The solution was then filtered and the solvent removed under reduced pressure to yield the desired polypyrrolidinophosphazenium fluoride.

Synthesis Example 7

The linear polyaminophosphazenium chloride of Synthesis Example 4.II (0.00327 moles) was charged to a three necked flask fitted with a thermometer and condenser. To this was added dimethyl sulfoxide (DMSO, 6 ml) and potassium trimethylsilanolate (0.00327 moles) and the reaction mixture stirred for two hours at 60° C. The DMSO was then removed under reduced pressure and the residue dissolved in dichloromethane (10 ml), upon which the solution was filtered. The solvent was then removed from the filtrate under reduced pressure to yield the desired poly (dimethylamino)phosphazenium trimethylsilanolate product.

Synthesis Example 8

The process of Synthesis Example 7 was repeated using the linear polyaminophosphazenium chloride of Synthesis Example 5.I to yield polypyrrolidinophosphazenium trimethylsilanolate.

Synthesis Example 9

The linear polyaminophosphazenium chloride of Synthesis Example 5.I (0.0010 moles) was charged to a three necked flask fitted with a thermometer and condenser. To this was added DMSO(5 ml) and sodium methoxide (0.0019 moles) and the reaction mixture stirred for twenty hours at room temperature. The DMSO was then removed under reduced pressure and the residue dissolved in methanol (20 ml), upon which the solution was filtered. The solvent was then removed from the filtrate under reduced pressure to yield the desired polypyrrolidinophosphazenium methoxide product.

Polymerization Example 13

90 g of octamethylcyclotetrasiloxane and log of linear polydimethylsiloxane fluid end-blocker with a viscosity of 100 mm$^2$/s, with a water content of approximately 60 ppm, were placed in a reaction vessel under nitrogen. The reaction mixture was heated to 100° C. and held for thirty minutes under reduced pressure (600 mbar) to remove dissolved $CO_2$. The reaction mixture was then placed under a nitrogen atmosphere, heated to 150° C. upon which 50 ppm of the linear polyaminophosphazenium trimethylsilanolate of Synthesis Example 7 was added. After 60 seconds the reaction mixture was neutralized yielding a polymer with a nonvolatile content (NVC) of 86.5%. After de-volatilization, a polymer with a viscosity of approximately 8,200 mm$^2$/s was obtained with a final NVC of 97.9%.

Polymerization Example 14

90g of octamethylcyclotetrasiloxane and 10g of polydimethylsiloxane end-blocker with a viscosity of 100 mm$^2$/s fluid, with a water content of approximately 60 ppm, were placed in a reaction vessel under nitrogen. The reaction mixture was heated to 100° C. and held for thirty minutes under reduced pressure (600 mbar) to remove dissolved $CO_2$. The reaction mixture was then placed under a nitrogen atmosphere, heated to 150° C. upon which 50 ppm of the linear polyaminophosphazenium fluoride of Synthesis Example 6 was added. After 60 seconds the reaction mixture was neutralized yielding a polymer with a NVC of 86.5%. After de-volatilization, a polymer with a viscosity of approximately 10,223 mm$^2$/s was obtained with a final NVC of 96.4%.

Polymerization Example 15

70 g of a silanol end-blocked polydimethylsiloxane having a viscosity of 14 mm$^2$/s and cyclodimethylsiloxane(25 g), and a polydimethyl siloxane end-blocker having a viscosity at 25° C. of 10 mm$^2$/s, (5 g) were mixed together in a reaction vessel and the reaction mixture heated to 135° C. and pressure of 500 mbar. At that temperature the linear polyaminophosphazenium trimethylsilanolate of Synthesis Example 7 (200 ppm) was added. After 15 minutes the reaction was cooled and neutralized prior to stripping for 1 hr at 160° C. under greatly reduced pressure. The final product had a viscosity at 25° C. of 1288 mm$^2$/s, a NVC of 96.90% and a residual silanol content of 85.7 ppm.

Polymerization Example 16

70 g of a silanol end-blocked polydimethylsiloxane having a viscosity of 14 mm$^2$/s and cyclodimethylsiloxane(25 g), and a polydimethyl siloxane end-blocker having a viscosity at 25° C. of 10 mm$^2$/s, (5 g) were mixed together in a reaction vessel and the reaction mixture heated to 135° C. and pressure of 600 mbar. At that temperature the linear polyaminophosphazenium fluoride of Synthesis Example 6 (180 ppm) was added. After 15 minutes the reaction was cooled and neutralized prior to stripping for 1 hr at 160° C. under greatly reduced pressure. The final product had a viscosity at 25° C. of 705 mm$^2$/s, a NVC of 99% and a residual silanol content of 104 ppm.

Polymerization Example 17

25 g of a silanol end-blocked polydimethylsiloxane having a viscosity of 14 mm$^2$/s and cyclodimethylsiloxane(70 g), and a polydimethyl siloxane end-blocker having a viscosity at 25° C. of 10 mm$^2$/s, (5 g) were mixed together in a reaction vessel and the reaction mixture heated to 130° C. and pressure of 600 mbar. At that temperature the linear polyaminophosphazenium trimethylsilanolate of Synthesis Example 8 (360 ppm) was added. After 30 minutes the reaction was cooled and neutralized prior to stripping for 1 hr at 160° C. under greatly reduced pressure. The final product had a viscosity at 25° C. of 1107 mm$^2$/s, a NVC of 97.6% and a residual silanol content of 60.3 ppm.

Synthesis Example 10

Toluene and a linear phosphonitrilic chloride, $[Cl^3PNCl_2PNPCl_3]^+PCl_6^-$ ($2.16 \times 10^{-3}$ moles) were charged to a three necked flask followed by dichlorobenzene (15 ml) under nitrogen. The reactor was cooled down to −15° C., and triethylamine added (0.078 mole) followed by a solution of dimethylamine hydrochloride (0.039 mole) in dichlorobenzene (35 ml). The reaction mixture was then heated and stirred at 150° C. for 24. The reaction mixture was cooled down and then filtered, after which the solvent was removed under reduce pressure. The liberation of base was carried out on a column of resin DOWEX 550A OH−, in excess, using methanol as the eluant. Overall yield of poly(dimethylamino)phosphazenium hydroxide was over 90%.

Polymerization Example 18

90 g of octamethylcyclotetrasiloxane and 10 g of polydimethylsiloxane end-blocker with a viscosity of 100 mm$^2$/s fluid, with a water content of approximately 60 ppm, were placed in a reaction vessel under nitrogen. The reaction mixture was heated to 100° C. and held for thirty minutes under reduced pressure (600 mbar) to remove dissolved $CO_2$. The reaction mixture was then placed under a nitrogen atmosphere, heated to 150° C. upon which 100 ppm of the linear polyaminophosphazenium hydroxide of Synthesis Example 10 was added. After 300 seconds the reaction mixture was neutralized yielding a polymer with a NVC of 86.8%. After de-volatilization, a polymer with a viscosity of approximately 9,800 mm$^2$/s was obtained with a final NVC of 98.9%.

Synthesis Example 11

To a three necked flask was charged pyrrolidine (0.0448 mole) and anhydrous dichloromethane (30 ml). The flask was cooled down to −700C and N-butyllithium 2.5M solution in hexane added dropwise (0.0448 mole). The obtained solution was withdrawn with a syringe and added at −50° C. into a second flask already charged with [$Cl_3PNCl_2PNPCl_3$]$^+$$PCl_6^-$ (2.6$10^{-3}$ mole) and anhydrous dichloromethane (20 ml). The reaction mixture was stirred for 1 hour and then allowed to warm to room temperature slowly over 2 hours. The lithium chloride salt was removed by filtration and the solvent removed under reduce pressure. Liberation of base was carried out on a column of resin DOWEX G55 Cl− prepared by washing it with a large quantity of KOH solution 1N, and water. A solution of methanol was used as eluant giving an overall yield of polypyrrolidinophosphazenium hydroxide of over 90%.

Polymerization Example 19

90 g of octamethylcyclotetrasiloxane and 10 g of polydimethylsiloxane end-blocker with a viscosity of 100 mm$^2$/s fluid, with a water content of approximately 60 ppm, were placed in a reaction vessel under nitrogen. The reaction mixture was heated to 100° C. and held for thirty minutes under reduced pressure (600 mbar) to remove dissolved $CO_2$. The reaction mixture was then placed under a nitrogen atmosphere, heated to 150° C. upon which 100 ppm of the linear polyaminophosphazenium hydroxide of Synthesis Example 11 was added. After 300 seconds the reaction mixture was neutralized yielding a polymer with a NVC of 85.9%. After de-volatilization, a polymer with a viscosity of approximately 9,780 mm$^2$/s was obtained with a final NVC of 98.7%.

That which is claimed is:

1. A process for making a linear phosphazene base catalyst comprising reacting a linear phosphonitrile halide compound with a compound selected from secondary amines and salts and metal amides thereof to form an aminated phosphazene material, followed by reacting the aminated phosphazene material in an ion exchange reaction replacing the anion of the aminated phosphazene material with a nucleophile.

2. A process according to claim 1, wherein the phosphonitrile halide is a phosphonitrile chloride.

3. A process according to claim 2, wherein a phosphonitrile chloride of the formula

where n is 1–10 and Z— is an anion selected from Cl— and PCl6—, is reacted with a secondary amine of the formula NR2, wherein each R independently denotes a hydrocarbon group having up to 10 carbon atoms or wherein the two R groups form with the N atom a heterocyclic group, to form the aminated phosphazene material, and the aminated phosphazene material formed is treated in an ion exchange reaction with a basic nucleophile to form a linear phosphazene base catalyst of the formula

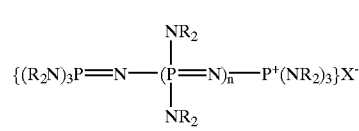

wherein X— denotes the anion of the basic nucleophile.

4. A process according to claim 3, wherein the secondary amine is selected from dimethylamine and pyrollidine.

5. A process according to claim 3, wherein the amination reaction between the phosphonitrile halide and the secondary amine is carried out in the presence of a material which is able to capture exchanged halides.

6. A process according to claim 1, wherein the ion exchange reaction is carried out by passing the aminated phosphazene material over an ion exchange resin.

7. A linear phosphazene base catalyst of the general formula (1),

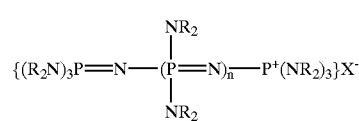

wherein R denotes a hydrocarbon having up to 10 carbon atoms or wherein the two R groups on each N atom form with the N atom a heterocyclic group, X is fluoride anion, and n has an average value of from 1.2 to 10.

8. A linear phosphazene base catalyst according to claim 7, wherein n has an average value of from 1.8 to 3.

* * * * *